(12) United States Patent
Elies et al.

(10) Patent No.: US 6,432,139 B1
(45) Date of Patent: Aug. 13, 2002

(54) MIDDLE EAR IMPLANT

(75) Inventors: Wolfgang Elies, Bielefeld; Carsten Dalchow, Düsseldorf, both of (DE)

(73) Assignee: Spiggle & Theis, Dieburg (DE)

(*) Notice: Subject to any disclaimer, the term of this patent is extended or adjusted under 35 U.S.C. 154(b) by 0 days.

(21) Appl. No.: 09/622,450

(22) PCT Filed: Jan. 29, 1999

(86) PCT No.: PCT/EP99/00574
§ 371 (c)(1),
(2), (4) Date: Aug. 17, 2000

(87) PCT Pub. No.: WO99/42060
PCT Pub. Date: Aug. 26, 1999

(30) Foreign Application Priority Data

Feb. 18, 1998 (DE) .................. 298 02 776 U

(51) Int. Cl.⁷ .................................. A61F 2/18
(52) U.S. Cl. ...................................... 623/10
(58) Field of Search ................. 623/10, 11.11

(56) References Cited

U.S. PATENT DOCUMENTS

| 3,710,399 A | | 1/1973 | Hurst |
| 4,510,627 A | | 4/1985 | Treace et al. |
| 4,601,723 A | * | 7/1986 | McGrew ............ 623/10 |
| 4,653,510 A | | 3/1987 | Koll |
| 4,740,209 A | * | 4/1988 | Gersdorff ........... 623/10 |
| 6,168,625 B1 | * | 1/2001 | Prescott ............ 623/10 |

FOREIGN PATENT DOCUMENTS

| DE | 392570 A1 | 2/1991 |
| DE | 29819892 U1 | 3/1999 |

* cited by examiner

Primary Examiner—David J Isabella
(74) Attorney, Agent, or Firm—Volpe and Koenig, P.C.

(57) ABSTRACT

Deafness is often caused by damage to the ossicular chain, which at present is partly or fully replaces by surgical implantation of a corresponding titanium prosthesis. Known versions of this type of middle ear implant consist of a flat coupling body (8) designed to rest against the ear drum, an oblong shank (3) connected to the body for bridging the tympanic cavity and a base (4,11) which is joined to the shank (3) and rests against the base of the implant in the tympanic cavity. Because the depth oft he tympanic cavity varies from patient to patient and measurements become known only during surgery, the length of the implant has to be adjusted very quickly. To be able to do this more simply than is possible with the known implants having a fixed length, the middle ear implant provided by the invention is characterized in that the oblong shank (3) has separation zones (6) to allow for individual adjustment of the shank length to the patient-specific depth of the tympanic cavity during the surgical intervention, and in that the base (4, 11) and/or the flat coupling body (1, 8) are embodied as a slide-on connector part which houses the corresponding end of the shank (3).

10 Claims, 3 Drawing Sheets

MIDDLE EAR IMPLANT

BACKGROUND

The present invention relates to a middle ear implant with a flat coupling body for application against the eardrum, an elongated shaft connected therewith for spanning the space in the tympanic cavity, and a shaft-connected base for application against the supporting point for the implant in the tympanic cavity.

Impaired hearing ranging up to deafness can have different pathological causes. One oft he causes typically lies in a disease-related change in or degeneration oft he small auditory bones of the ossicular chain in the middle ear, i.e., the three ossicles positioned in the tympanic cavity (Cavum tympani): the hammer, the anvil, and the stirrup.

These ossicles carry sound transmission from the eardrum via the vestibule window (vestibular window) to the inner ear, the air in the middle ear making possible almost friction-free vibration of the ossicles combined together in articulated fashion. These articulated ossicles represent a lever mechanism which amplifies the recorded sound waves in the case of humans by about two to three times. If the lever mechanism is disturbed, e.g., through a degenerative change in the bone substance, a person will become hard of-hearing.

It is known to totally or partially replace the damaged ossicular chain surgically with an implanted auditory-bone prosthesis, called a middle ear implant. This typically includes a disk-shaped coupling body for application against the eardrum, an elongated shaft connected thereto for spanning the free space in the tympanic cavity which results from the surgically removed or no longer present ossicles, and an implant shoe for broad-surface application against the supporting plate for the stirrup upon replacement of all three bones (total implant) or an implant bell for application against the stirrup (stapes) with the no longer present hammer and anvil (partial implant). The middle ear implant then completely or partially takes over the transmission of vibrations from the eardrum to the vestibule window so that the patient again attains a normal hearing capacity.

The various known middle ear implants differ essentially in their structural design and in the selection of materials.

U.S. Pat. No. 4,510,627 refers to an auditory-bone prosthesis made of a porous plastic (polyethylene) with a metallic core of high sound conductivity. The porous material is intended to serve a unifying joining of the implant to the ear drum and the supporting plate while the metallic core takes over the function of sound transmission.

Also known are middle ear implants made of ceramics. These have the disadvantage, however, of being relatively bulky and reacting rather sluggishly with a weight of about 40 mg. In addition, in the case of certain ceramics, the possibility exists for complete destruction through recurring middle ear inflammations. For this reason, DE 39 01 796 A1 provides a middle ear implant made of gold, with the disk-shaped coupling body and the base made of pure gold and a gold wire as the shaft. is It is also known from DE 42 10 235 C1 to provide a middle ear implant in which the flat coupling body for application against the eardrum is made of titanium coated with a bioactive titanium oxide layer. The shaft is made of pure gold, and the implant shoe is again made of titanium.

In all of these middle ear implants, a principal problem exists in the fact that the depth of the tympanic cavity to be bridged by the implant or a portion thereof differs from patient to patient, with the limiting condition that the precise length can only be determined for the first time during surgical intervention. An implant with a patient-specific length-adapted shaft must therefore be available very quickly.

For this purpose, the above-mentioned DE 39 01 796 A1 provides for the formation oft a curved region in the shaft, which forms a reserve length and permits adjusting the overall length of the shaft to individual circumstances during surgical intervention. However, since the middle ear implant is extremely small, the length adjustment requires a considerable degree of dexterity. Also, the stability of the adjusted shaft length is not always ensured.

As a result, a number of middle ear implants with shafts of different length are currently typically kept on hand during surgery. The implant coming closest to the individual requirements is then selected. This method has the disadvantage of a considerable logistical effort with respect to the production, storage, and maintaining a ready supply of a number of middle,ear implants with shafts of different length.

SUMMARY

The object oft he present invention is to improve the middle ear implant described above such that adaptation oft he length of the shaft oft he middle ear implant to patient-specific requirements is possible in a simple but effective manner.

The solution to this problem is attained according to the present invention in that the elongated shaft possesses potential separation points for individual adaptation oft he length oft he shaft to the patient-specific depth oft he space oft he tympanic cavity during surgical intervention and in that the base and/or the flat coupling body is formed as of a slide-on connector part accepting the corresponding end of the shaft.

The middle ear implant of the present invention can therefore be adapted very rapidly during surgical intervention to the patient-specific depth of the space of the tympanic cavity by simply breaking off the excess length of the shaft, with the base or the flat coupling body subsequently being mounted on the free end of the shaft.

According to a first further development, the middle ear implant can be designed such that the flat coupling body is joined as one piece with the shaft, and the base, having the form of a shoe for broad-surface application against the supporting plate for the stirrup, is designed as a slide-on connector part.

In this case, the implant serves as a total prosthesis, i.e., it replaces the entire ossicular chain.

The implant shoe therefore has three functions in the case of the middle ear implant according to the present invention:
1. Through its base, it is designed to ensure broad-surface application against the supporting plate for the stirrup (stapes), i.e., to avoid tipping in order to guarantee a stable position of the middle ear implant.
2. Because of its broad base, i.e., as a result of the enlarged surface area, a lower pressure is exerted on the supporting plate.
3. It covers the broken-off edge like a cap and therefore avoids the need for refinishing the current actual separation point.

According to a second further development of the present invention, the middle ear implant is designed such that the flat coupling body is formed as a slide-on connector part while the base, in the form of a bell for application against the stirrup, is joined as one piece with the shaft. In this case, the implant serves as a partial prosthesis, i.e., replaces only the anvil and the hammer.

According to a further development of the present invention, the potential separation points are formed at a predetermined mutual distance from each other, special advantages being attained if the mutual distances of the potential separation points are constant over the extent of the shaft through specification of a modular dimension.

Such a design advantageously permits stocking two types of implants whose shaft length differs by a predetermined fraction of the repeat measurement, preferably by half oft he modular dimension. Advantageously, it is then possible to have length adaptations down to one half of the modular dimension.

All oft he parts of the middle ear implant preferably consist of titanium. Titanium is a material which is lightweight, biocompatible, and a good transmitter of sound.

At least the flat coupling body and the shoe are preferably coated with a bone-like substance, preferably hydroxylapatite. Such a construction advantageously permits very intimate joining of the implant to the eardrum and the supporting plate, with the roughening of the surface of the implant parts being necessary.

According to another refinement of the present invention, the flat coupling body is formed as a disk. The disk exhibits symmetrically distributed circular openings. Such a refinement very advantageously permits very intimate intergrowth oft he ear drum with the coupling body.

According to a further development of the present invention, the flat coupling body with attached shaft, on the one hand, and the implant shoe, on the other, are manufactured in engineering production as turned parts.

In contrast to the middle ear implants according to the state of the art cited above, which sometimes need to be manufactured via troublesome manual labor, the middle ear implant according to the present invention can be produced by machining on an automatic lathe.

BRIEF DESCRIPTION OF THE DRAWINGS

Further refinements and advantages of the present invention follow from the description of the embodiments of the invention represented in the drawings.

These include.

DETAILED DESCRIPTION OF THE PREFERRED EMBODIMENTS

Figure 1:
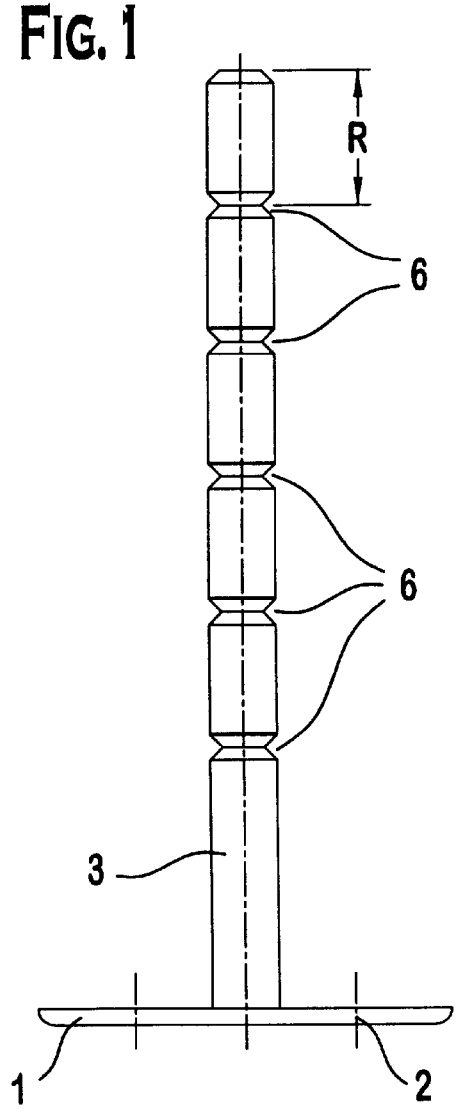
FIG. 1 is an side view of a first embodiment of a middle ear implant according to the present invention with potential separation points formed on the shaft, whose mutual distances are constant over the extent of the shaft through specification of a modular dimension, and with a disk-shaped flat coupling body joined as one piece with the shaft and designed for application a against the eardrum.
Figure 3:
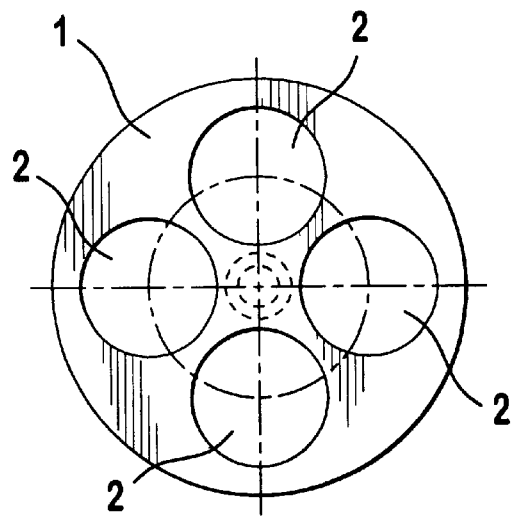
FIG. 3 is a top view of the disk-shaped flat coupling body according to FIG. 1 or FIG. 2.
Figure 4:
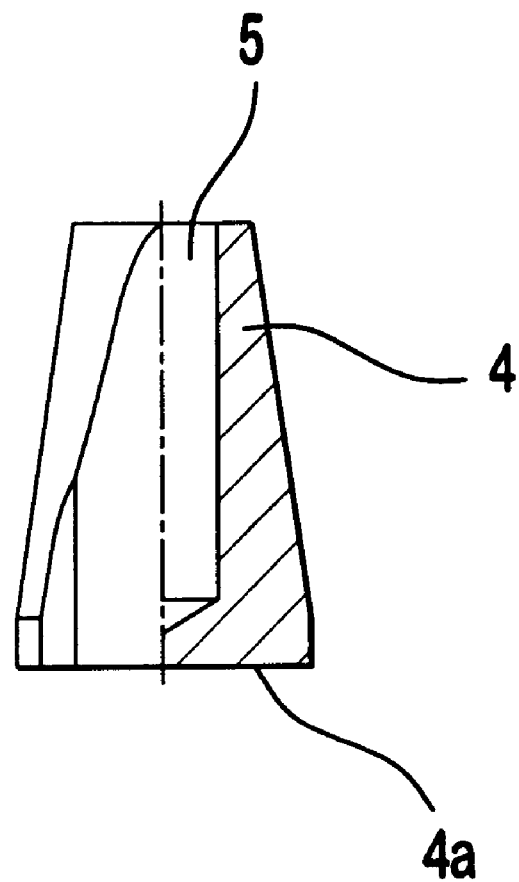
FIG. 4 is a view, partially in cross-section, of the implant shoe, which is formed as a slide-on connector part that receives the free end of the shaft.
Figure 5:
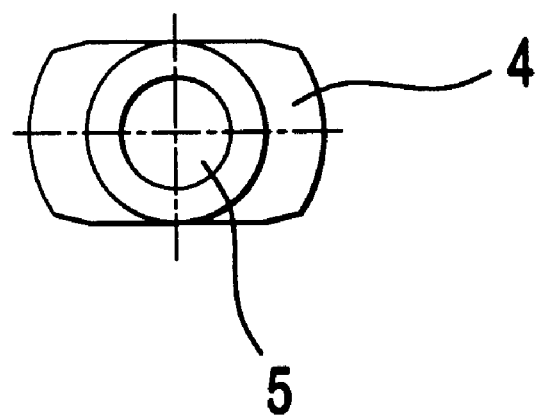
FIG. 5 is a top view of the base according to FIG. 4.

FIGS. 1 and 4 in conjunction with the top views according to FIGS. 3 and 5 show an initial embodiment of the middle ear implant according to the present invention which is preferably employed in replacing all of the ossicles. It includes a flat coupling body which is formed in the embodiment as a disk 1. The disk 1 is used for application against the eardrum of a hearing-impaired patient and includes in the represented embodiment four symmetrically arranged circular boreholes 2 through which eardrum substance can w following implantation in order thus to ensure reliable anchoring of the flat coupling body, the disk 1, against the eardrum. Joined as one piece with coupling disk 1 is an elongated shaft 3 which serves to span the space in the tympanic cavity. The free (upper) end of elongated shaft 3 can be covered by an implant shoe for broad-surface application against the supporting plate for the stirrup (stapes) of the hearing-impaired patient. For this purpose, the shoe 4 according to FIG. 4 is formed as a slide-on connector part with an opening 5 in which the free end of shaft 3 can be inserted. This base 4 has three functions:

1. Through the relatively large bottom surface 4a, which, following implantation, comes to be applied against the supporting plate for the stirrup, tipping of the middle ear implant is prevented, i.e., the base aids the stability of the implant.
2. Through the relatively large bottom surface 4a, only a relatively low pressure is exerted on the supporting plate.
3. Finally, the shoe 4 serves in covering the edges at the free end of shaft 3, as will be explained in detail below.

According to the present invention, the elongated shaft 3 possesses several potential separation points 6 for individual adaptation of the length of the shaft to the patient-specific depth of the space of the tympanic cavity during surgical intervention. For this purpose, the individual excess length of the shaft is simply broken off, with the edges at the break subsequently being covered by mounted shoe 4.

As shown in FIG. 1, the potential separation points 6 are formed at a predetermined mutual distance from each other. The mutual distances of potential separation points 6 in this embodiment are constant over the extent of the shaft through the specification of a modular dimension R. The modular dimension R is specified as a function of the selected material such that the excess length of material can be broken off at the separation point 6 involved without adversely affecting the other parts of shaft 3.

Figure 2:
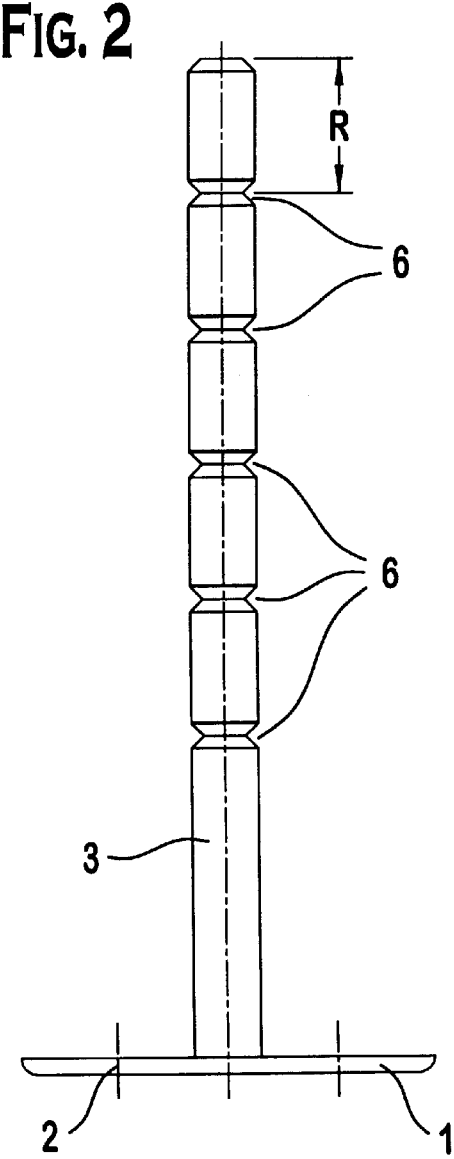
FIG. 2 is a view of a middle ear implant similar to FIG. 1, in which, however, the shaft length is increased by half the modular dimension.

In order to be able to deal in very simple fashion with still smaller patient-specific differences in the dimensions oft he tympanic cavity, a second type of middle ear implant is advantageously provided as shown in FIG. 2, which differs from the implant according to FIG. 1 only in the fact that the length of the shaft 3 is greater by one half oft he modular dimension. As a result, shaft lengths differing by one half oft he modular dimension can be very simply provided.

Preferably, both disk 1 and shaft 3 attached thereto as well as base 4 are formed from titanium. Titanium is a material which is lightweight, biocompatible, and a good transmitter of sound. Basically, however, other biocompatible materials can also be employed. Both coupling disk 1 as well as shoe 4 are preferably coated with a bone-like substance, preferably hydroxylapatite. In this way, a very intensive joining of the implant to the eardrum can be attained, on the one hand, and to the supporting plate, on the other. The surface of the disk and the base are preferably roughened.

In the embodiment according to FIGS. 1 and 2, the flat coupling body is formed as a disk 1. Other embodiments are conceivable here, too, for example, the forming of the coupling body as a spoked wheel.

As can be seen from the figures, both the coupling body with the attached shaft 3, on the one hand, and the implant shoe 4, on the other, are produced as turned parts so that the middle ear implant according to the present invention can be produced as machined parts using an automatic lathe, in contrast to known implants, which sometimes require troublesome manual labor.

The middle ear implant represented in FIGS. 1–5 typically has the following dimensions:

Diameter of disk 1: 3 mm at a disk thickness of 0.15 mm.

Diameter of shaft 3 is approximately 0.4 mm.

Modular dimension R is approximately 1 mm.

The length of shaft 3 is approximately 7 mm in the design according to FIG. 1, but to 7.5 mm in the design according to FIG. 2.

The diameter of boreholes 2 is approximately 1 mm.

The height of shoe 4 is approximately 2 mm with a blind borehole 5 having a length of 1.7 mm.

The bottom surface 4a of the shoe is approximately 1.3 mm at a shoe width of 0.8 mm.

If the shaft diameter is less than 0.4 mm, e.g., 0.2 or 0.3 mm, then the indentations in shaft 3 forming the potential separation points 6 are less pronounced. In addition to the function that the shaft should break more easily at these potential separation points or can be separated there, the potential separation points generally have the additional function that a reduced shaft diameter is present at these points, which should facilitate the mounting of the implant shoe. In general, therefore, one speaks of a potential separation point which can also be characterized as a potential break point in the case of thicker shafts and manual breaking off.

In the first embodiment of the present invention according to FIGS. 1–5, the disk-shaped coupling body 1 is joined as one piece with shaft 3, and shoe 4 is formed as a separate part which can be mounted on shaft 3 while covering the break edges.

The present invention can also involve a design in which the disk-shaped coupling body is formed as a separate part which can be mounted on the shaft, covering the edges at the break. The shoe is then preferably joined as one piece with the shaft, but can alternatively also be formed as a slide-on connector part, as shown in FIGS. 1–5.

Such an embodiment is then especially advantageous if only some of the ossicles (the hammer and the anvil) need to be replaced by a partial prosthesis. In such cases, the shoe, e.g., is replaced by a bell-shaped base, which is typically joined as one piece with the shaft. Other forms of the shoe are also conceivable.

Figure 6:
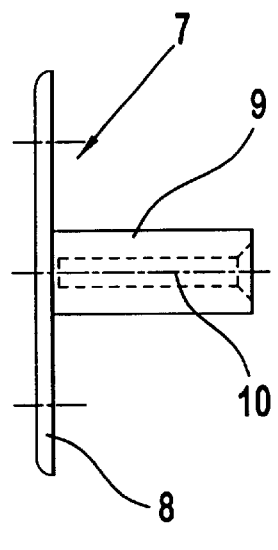
FIG. 6 is a side view of a second embodiment of the present invention according to FIG. 1 or 2, however, with a shaft-mountable disk-shaped coupling body for application against the eardrum.
Figure 7:
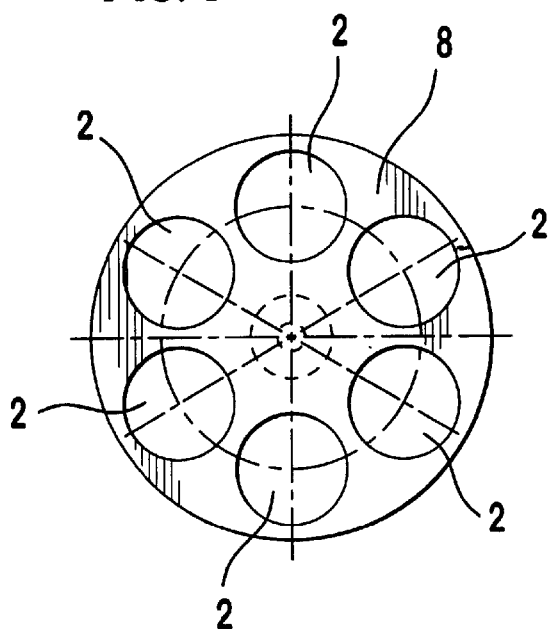
FIG. 7 is a top view of the coupling body according to FIG. 6.

The view according to FIG. 6 together with the top view according to FIG. 7 shows a mountable disk-shaped coupling body 7 with a disk 8 rounded off at the periphery. The disk, in the embodiment shown, has six openings 2 for intergrowth with the eardrum, and to which is attached as one piece a stub 9 with a chamfered borehole 10 for accepting the shaft according to FIG. 1 or FIG. 2.

Figure 8:
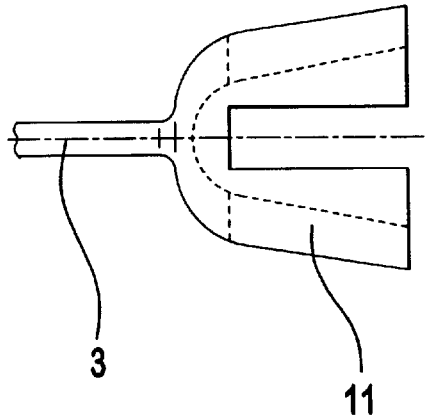
FIG. 8 is a side view of a bell-shaped base joined as one piece with the shaft.
Figure 9:
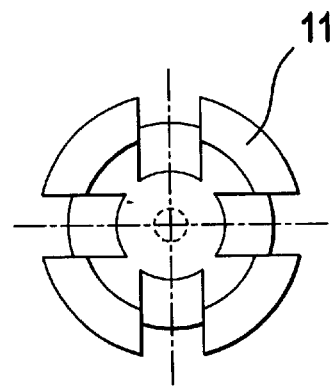
FIG. 9 is a plan view of the underside of the base.

The sectional view according to FIG. 8 together with the plan view of the bottom according to FIG. 9 shows the bell-shaped base 11, which is segmented for better fitting to the shape of the stirrup and which is secured as one piece to shaft 3, but can also be formed, in principle, as a mountable piece.

Everything which has been said about the embodiment according to FIGS. 1–5 concerning the disk-shaped coupling body 1, shaft 3, and shoe 4 applies correspondingly for disk-shaped coupling body 8 according to FIG. 6 and unseparated shaft 3 and bell 11 according to FIG. 8.

The implant shown in FIGS. 6–9 typically includes the following dimensions, which likewise are only exemplary. The diameter and thickness of disk 8 correspond to those of disk 1. The diameter of boreholes 2 is in each case approximately 0.76 mm. The stub 9 has a length of 1.6 mm, with a diameter of 0.6 mm. Since, in the case of a partial prosthesis, the shaft 3 can be thinner, in the present case it is about 0.3 mm; the diameter of interior blind borehole 10 in stub 9 is then also correspondingly narrower. In the case of such a thin shaft 3, the indentations at the potential separation points are only minimally realized since, in the case of such a thin shaft, it is not so much a matter of increasing the ease of breaking, but of reducing the diameter for ease of mounting disk 8, which is aided by chamfering the blind borehole 10.

The height of bell 11 amounts to 1.5 mm at a bottom diameter of about 1.7 mm.

It is sometimes necessary during an implantation to incline disk-shaped coupling body 1 or 8 with respect to shaft 3 in order to take into account the given anatomy of a patient's ear. In order to facilitate this deflection, shaft 3 is appropriately formed to be narrower in the area of disk attachment than elsewhere.

What is claimed is:

1. Middle ear implant comprising a flat coupling body (1,8) for application against an eardrum, an elongated shaft (3) connected therewith for spanning a space in the tympanic cavity, and a base (4,11) connected with the shaft (3) for application against a supporting point for the implant in the tympanic cavity, characterized in that the elongated shaft (3) includes a plurality of spaced separation points (6) for individual adaptation of the length of the shaft to a patient-specific depth of the space of the tympanic cavity during surgical intervention and that at least one of the base (4,11) and the flat coupling body (1,8) is adapted to be slidably connected to a corresponding end of the shaft (3) and engage at least one spaced discrete separation point when the patient-specific depth is determined.

2. Middle ear implant according to claim 1, characterized in that the flat coupling body (1) is adapted to be slidably connected to the shaft and the flat coupling body defines a broad surface for engaging a supporting plate for the stirrup.

3. Middle ear implant according to claim 1, characterized in that the flat coupling body (8) is adapted to be slidably connected to the shaft, and the base is bell-shaped (11) for application against the stirrup and is joined as one piece with the shaft (3).

4. Middle ear implant according to claim 1, characterized in that the plurality of spaced separation points (6) are formed at a predetermined mutual distance from each other.

5. Middle ear implant according to claim 4, characterized in that the distance between each oft he plurality of separation points is constant over the length of the shaft.

6. Middle ear implant according to claim 1, characterized in that the flat coupling body is formed as a disk (1).

7. Middle ear implant according to claim 6, characterized in that the disk (1) includes circular openings symmetrically distributed therein.

8. Middle ear implant kit comprising a flat coupling body for application against an eardrum, a base for application against a supporting point in the tympanic cavity, and an elongated shaft for spanning a space in the tympanic cavity between said body and said base, characterized in that the elongated shaft includes a plurality of spaced separation points for individual adaptation of the length oft he shaft to a patient-specific depth of the space of the tympanic cavity during surgical intervention and that at least one of the base and the flat coupling body is adapted to be slidably connected to a corresponding end of the shaft and engage at least one spaced discrete separation point when the patient-specific depth is determined.

9. Middle ear implant kit according to claim 8, characterized in that a second shaft of a different length than the elongated shaft and having a plurality of spaced separation points is provided.

10. Middle ear implant kit according to claim 9, characterized in that the difference in the lengths of the elongated shaft and the second shaft, respectively, is equal to one half of the distance between each oft he plurality of separation points oft he elongated shaft.

* * * * *